US007060816B2

(12) United States Patent
Barnett et al.

(10) Patent No.: US 7,060,816 B2
(45) Date of Patent: Jun. 13, 2006

(54) DETECTION OF FUNGAL PATHOGENS USING THE POLYMERASE CHAIN REACTION

(75) Inventors: Charles Jason Barnett, Research Triangle Park, NC (US); James Joseph Beck, Research Triangle Park, NC (US); Christy Violet Perry, Apex, NC (US)

(73) Assignee: Syngenta Participations AG, Basel (CH)

( * ) Notice: Subject to any disclaimer, the term of this patent is extended or adjusted under 35 U.S.C. 154(b) by 393 days.

(21) Appl. No.: 10/623,880

(22) Filed: Jul. 21, 2003

(65) Prior Publication Data

US 2004/0029255 A1 Feb. 12, 2004

Related U.S. Application Data

(62) Division of application No. 09/939,379, filed on Aug. 24, 2001, now Pat. No. 6,645,720.

(60) Provisional application No. 60/274,540, filed on Mar. 9, 2001.

(51) Int. Cl.
C07H 21/04 (2006.01)
C12Q 1/68 (2006.01)
C12P 19/34 (2006.01)

(52) U.S. Cl. .................. 536/24.33; 435/6; 435/91.1; 435/91.2; 536/24.3; 536/24.32; 536/24.33

(58) Field of Classification Search .................. None
See application file for complete search history.

(56) References Cited

U.S. PATENT DOCUMENTS

| 4,683,195 | A | | 7/1987 | Mullis et al. | |
|---|---|---|---|---|---|
| 4,683,202 | A | | 7/1987 | Mullis | |
| 5,585,238 | A | | 12/1996 | Ligon et al. | |
| 5,800,997 | A | * | 9/1998 | Beck | 435/6 |
| 5,955,274 | A | | 9/1999 | Ligon et al. | |

OTHER PUBLICATIONS

Schnabel et al., "Characterization of Ribosomal DNA from Venturia inaequalis and Its Phylogenetic Relationship to rDNA from Other Tree-Fruit Venturia Species," Phytopathology, 1999, vol. 89, No. 1, pp. 100-108.*
Sequence Alignment.*
Adaskaveg, J.E. and Hartin, R.J., *Characterization of Colletotrichum acutatum Isolates Causing Anthracnose of Almond and Peach in California Etiology*, vol. 87, No. 9 (1997), pp. 979-987.
Barker, I., et al. "Strawberry Blackspot Disease (*Colletotrichum acutatum*)" in Schots A., Dewey FM, Oliver R. (Eds.). *Modern assay for plant pathogenic fungi: identification, detection and quantification* (Wallingford, Oxford: CAB International, 1994), pp. 179-182.
Förster, H. and Adaskaveg, J.E., *Identification of Subpopulations of Colletotrichum acutatum and Epidemiology of Almond Anthracnose in California Phytopathology*, vol. 89, No. 11 (1999), pp. 1056-1065.
Johanson, A. and Jeger M. *Use of PCR for detection of Mycosphaerella fijiensis and M. musicola, the causal agents of Sigatoka leaf spots in banana and plantain Mycological Research*, vol. 97, No. 6 (1993), pp. 670-674.
Lee, et al. *A rapid, high yield mini-prep method for isolation of total genomic DNA from fungi Fungal Genetics Newsletter*, No. 35 (Jun., 1988), pp. 23-24.
Lee, S.B. and Taylor, J.W., "Isolation of DNA from fungal mycelia and single spores." In: eds. Innis, et al., *PCR Protocols: A Guide to Methods and Applications* (New York, Academic Press, Inc., 1990) pp. 282-287.
Mills, P.R., et al. "Detection of the Anthracnose Pathogen *Colletotrichum*" in Schots A., Dewey FM, Oliver R. (Eds.). *Modern assay for plant pathogenic fungi: identification, detection and quantification (Wallingford, Oxford: CAB International, 1994)*, pp. 183-189.
Nazar, et al. *Potential use of PCR-amplified ribosomal intergenic sequences in the detection and differentiation of verticillium wilt pathogens Physiological and Molecular Plant Pathology*, vol. 39, (1991), pp. 1-11.
Pryor, B.M. and Gilbertson, R.L. *Molecular phylogenetic relationships amongst Alternaria species and related fungi based upon analysis of nuclear ITS and mt SSU rDNA sequences* Mycological Research, vol. 104, Part 11 (Nov. 2000), pp. 1312-1321.
Schesser, K., et al. *Use of Polymerase Chain Reaction to Detect the Take-All Fungus, Gaeumannomyces graminis, in Infected Wheat Plants Applied and Environmental Microbiology*, vol. 57, No. 2 (1990), pp. 553-556.
Schnabel, G. et al. *Characterization of Ribosomal DNA from Venturia inaequalis and Its Phylogenetic Relationship to rDNA from Other Tree-Fruit Venturia Species Phytopathology*, vol. 89, No. 1 (1999), pp. 100-108.

(Continued)

Primary Examiner—Young J. Kim
(74) Attorney, Agent, or Firm—Mary Kakefuda

(57) ABSTRACT

The present invention relates to the use of primers in polymerase chain reaction assays for the detection of fungal pathogens Colletotrichum acutatum, Alternaria spp., and Cladosporium carpophilum. Specific primers are identified as being useful for the identification of fungal isolates using PCR based techniques. Also described are novel extraction buffer solutions for use in isolating DNA from an organism, methods of extracting DNA from tissue, and methods of performing PCR analysis on DNA extracted from tissue.

3 Claims, No Drawings

OTHER PUBLICATIONS

Sreenivasaprasad, S., et al. *Phylogeny and systematics of 18 Colletotrichum species based on ribosomal DNA spacer sequences Genome*, vol. 39 (1996), pp. 499-512.

Teviotdale, B.L., et al. *First Report of Alternaria Leaf Spot of Almond Caused by Species in the Alternaria alternata Complex in California Plant Disease*, vol. 85, No. 5 (May, 2001), pp. 558.

Wang et al, *PCR amplification from single seeds, facilitating DNA marker-assisted breeding Nucleic Acids Research*, vol. 21, No. 10 (1993), pp. 2527.

White, et al. "Amplification and direct sequencing of fungal ribosomal RNA genes for phylogenetics." In: eds. Innis, et al., *PCR Protocols: A Guide to Methods and Applications* (New York, Academic Press, Inc., 1990) pp. 315-322.

Zur, et al. *Development of a Polymerase Chain Reaction-Based Assay for the Detection of Alternaria Fungal Contamination in Food Products Journal of Food Protection*, vol. 62, No. 10 (1999), pp. 1191-1197.

GenBank Accession No. AF065849 [online], retrieved on Oct. 26, 2001. Retrieved from the Internet: <URL: http://www.ncbi.nlm.nih.gov>.

GenBank Accession No. AF071346 [online], retrieved on Oct. 26, 2001. Retrieved from the Internet: <URL: http://www.ncbi.nlm.nih.gov>.

GenBank Accession No. AF090853 [online], retrieved on Oct. 26, 2001. Retrieved from the Internet: <URL: http://www.ncbi.nlm.nih.gov>.

GenBank Accession No. AF090854 [online], retrieved on Oct. 26, 2001. Retrieved from the Internet: <URL: http://www.ncbi.nlm.nih.gov>.

GenBank Accession No. AF090855 [online], retrieved on Oct. 26, 2001. Retrieved from the Internet: <URL: http://www.ncbi.nlm.nih.gov>.

GenBank Accession No. AF218791 [online], retrieved on Oct. 26, 2001. Retrieved from the Internet: <URL: http://www.ncbi.nlm.nih.gov>.

GenBank Accession No. AF229459 [online], retrieved on Oct. 26, 2000. Retrieved from the Internet: <URL: http://www.ncbi.nlm.nih.gov>.

GenBank Accession No. AF229460 [online], retrieved on Oct. 26, 2001. Retrieved from the Internet: <URL: http://www.ncbi.nlm.nih.gov>.

GenBank Accession No. AF229461 [online], retrieved on Oct. 26, 2001. Retrieved from the Internet: <URL: http://www.ncbi.nlm.nih.gov>.

GenBank Accession No. AJ276055 [online], retrieved on Oct. 26, 2001. Retrieved from the Internet: <URL: http://www.ncbi.nlm.nih.gov>.

GenBank Accession No. AJ276059 [online], retrieved on Oct. 26, 2000. Retrieved from the Internet: <URL: http://www.ncbi.nlm.nih.gov>.

GenBank Accession No. Z73765 [online], retrieved on Oct. 26, 2001. Retrieved from the Internet: <URL: http://www.ncbi.nlm.nih.gov>.

GenBank Accession No. Z73786 [online], retrieved on Oct. 26, 2001. Retrieved from the Internet: <URL: http://www.ncbi.nlm.nih.gov>.

GenBank Accession No. Z73781 [online], retrieved on Oct. 26, 2001. Retrieved from the Internet: <URL: http://www.ncbi.nlm.nih.gov>.

GenBank Accession No. Z73799 [online], retrieved on Oct. 26, 2001. Retrieved from the Internet: <URL: http://www.ncbi.nlm.nih.gov>.

\* cited by examiner

SEQUENCE LISTING

<160> NUMBER OF SEQ ID NOS: 30

<210> SEQ ID NO 1
<211> LENGTH: 19
<212> TYPE: DNA
<213> ORGANISM: artificial sequence
<220> FEATURE:
<221> NAME/KEY: misc_feature
<222> LOCATION: (1)..(19)
<223> OTHER INFORMATION: Primer ITS1

<400> SEQUENCE: 1
tccgtaggtg aacctgcgg                                               19

<210> SEQ ID NO 2
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer ITS2

<400> SEQUENCE: 2
gctgcgttct tcatcgatgc                                              20

<210> SEQ ID NO 3
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer ITS3

<400> SEQUENCE: 3
gcatcgatga agaacgcagc                                              20

<210> SEQ ID NO 4
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Pimer ITS4

<400> SEQUENCE: 4
tcctccgctt attgatatgc                                              20

<210> SEQ ID NO 5
<211> LENGTH: 17
<212> TYPE: DNA
<213> ORGANISM: artificial sequence
<220> FEATURE:
<221> NAME/KEY: misc_feature
<222> LOCATION: (1)..(17)
<223> OTHER INFORMATION: Primer FORWARD

<400> SEQUENCE: 5
gtaaaacgac ggccagt                                                 17

<210> SEQ ID NO 6
<211> LENGTH: 17
<212> TYPE: DNA
<213> ORGANISM: artificial sequence

```
<220> FEATURE:
<221> NAME/KEY: misc_feature
<222> LOCATION: (1)..(17)
<223> OTHER INFORMATION: Primer REVERSE

<400> SEQUENCE: 6
caggaaacag ctatgac                                                  17

<210> SEQ ID NO 7
<211> LENGTH: 23
<212> TYPE: DNA
<213> ORGANISM: artificial sequence
<220> FEATURE:
<221> NAME/KEY: misc_feature
<222> LOCATION: (1)..(23)
<223> OTHER INFORMATION: Primer CaINT-1

<400> SEQUENCE: 7
ggcgccggcc cccaccacgg gga                                           23

<210> SEQ ID NO 8
<211> LENGTH: 22
<212> TYPE: DNA
<213> ORGANISM: artificial sequence
<220> FEATURE:
<221> NAME/KEY: misc_feature
<222> LOCATION: (1)..(22)
<223> OTHER INFORMATION: Primer CaINT-2

<400> SEQUENCE: 8
ggcgccggcc ccgtcacggg gg                                            22

<210> SEQ ID NO 9
<211> LENGTH: 17
<212> TYPE: DNA
<213> ORGANISM: artificial sequence
<220> FEATURE:
<221> NAME/KEY: misc_feature
<222> LOCATION: (1)..(17)
<223> OTHER INFORMATION: Primer CaInt2

<400> SEQUENCE: 9
ggggaagcct ctcgcgg                                                  17

<210> SEQ ID NO 10
<211> LENGTH: 17
<212> TYPE: DNA
<213> ORGANISM: artificial sequence
<220> FEATURE:
<221> NAME/KEY: misc_feature
<222> LOCATION: (1)..(17)
<223> OTHER INFORMATION: Primer CaInt2

<400> SEQUENCE: 10
cgggcagggg aagcctc                                                  17

<210> SEQ ID NO 11
<211> LENGTH: 17
<212> TYPE: DNA
<213> ORGANISM: artificial sequence
<220> FEATURE:
<221> NAME/KEY: misc_feature
<222> LOCATION: (1)..(17)
<223> OTHER INFORMATION: Primer JB677

<400> SEQUENCE: 11
ggaagcctct cgcgggc                                                  17
```

<210> SEQ ID NO 12
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer JB678

<400> SEQUENCE: 12
atcccagtgc gagacgttag                                                 20

<210> SEQ ID NO 13
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer Alal-1

<400> SEQUENCE: 13
aaatatgaag gcgggctgga                                                 20

<210> SEQ ID NO 14
<211> LENGTH: 25
<212> TYPE: DNA
<213> ORGANISM: artificial sequence
<220> FEATURE:
<221> NAME/KEY: misc_feature
<222> LOCATION: (1)..(25)
<223> OTHER INFORMATION: Primer Alal-2

<400> SEQUENCE: 14
agacctttgc tgatagagag tgcga                                           25

<210> SEQ ID NO 15
<211> LENGTH: 25
<212> TYPE: DNA
<213> ORGANISM: artificial sequence
<220> FEATURE:
<221> NAME/KEY: misc_feature
<222> LOCATION: (1)..(25)
<223> OTHER INFORMATION: Primer Alal-3

<400> SEQUENCE: 15
cctttgctga tagagagtgc gactt                                           25

<210> SEQ ID NO 16
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer Alal-4

<400> SEQUENCE: 16
ctcggggtta cagccttgct                                                 20

<210> SEQ ID NO 17
<211> LENGTH: 25
<212> TYPE: DNA
<213> ORGANISM: artificial sequence
<220> FEATURE:
<221> NAME/KEY: misc_feature
<222> LOCATION: (1)..(25)
<223> OTHER INFORMATION: Primer Ala-5

```
<400> SEQUENCE: 17
aacctctcgg ggttacagcc ttgct                                    25

<210> SEQ ID NO 18
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer Alal-6

<400> SEQUENCE: 18
tgatagagag tgcgacttgt                                          20

<210> SEQ ID NO 19
<211> LENGTH: 21
<212> TYPE: DNA
<213> ORGANISM: artificial sequence
<220> FEATURE:
<221> NAME/KEY: misc_feature
<222> LOCATION: (1)..(21)
<223> OTHER INFORMATION: Primer Alt1

<400> SEQUENCE: 19
attgcaatca gcgtcagtaa c                                        21

<210> SEQ ID NO 20
<211> LENGTH: 21
<212> TYPE: DNA
<213> ORGANISM: artificial sequence
<220> FEATURE:
<221> NAME/KEY: misc_feature
<222> LOCATION: (1)..(21)
<223> OTHER INFORMATION: Primer Alt2

<400> SEQUENCE: 20
caagcaaagc ttgagggtac a                                        21

<210> SEQ ID NO 21
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer Vcarp1

<400> SEQUENCE: 21
tgccggaatc agcaagccct                                          20

<210> SEQ ID NO 22
<211> LENGTH: 16
<212> TYPE: DNA
<213> ORGANISM: artificial sequence
<220> FEATURE:
<221> NAME/KEY: misc_feature
<222> LOCATION: (1)..(16)
<223> OTHER INFORMATION: Primer Vcarp2

<400> SEQUENCE: 22
caaccgcggc ccggat                                              16

<210> SEQ ID NO 23
<211> LENGTH: 20
<212> TYPE: DNA
<213> ORGANISM: artificial sequence
```

```
<220> FEATURE:
<221> NAME/KEY: misc_feature
<222> LOCATION: (1)..(20)
<223> OTHER INFORMATION: Primer Vcarp3

<400> SEQUENCE: 23
tcagcaagcc ctgcctagaa                                                   20

<210> SEQ ID NO 24
<211> LENGTH: 22
<212> TYPE: DNA
<213> ORGANISM: artificial sequence
<220> FEATURE:
<221> NAME/KEY: misc_feature
<222> LOCATION: (1)..(22)
<223> OTHER INFORMATION: Primer Vcarp4

<400> SEQUENCE: 24
gtctgaggag aaagccaaac ga                                                22

<210> SEQ ID NO 25
<211> LENGTH: 16
<212> TYPE: DNA
<213> ORGANISM: artificial sequence
<220> FEATURE:
<221> NAME/KEY: misc_feature
<222> LOCATION: (1)..(16)
<223> OTHER INFORMATION: Primer Vcarp5

<400> SEQUENCE: 25
gctccgggcg agggat                                                       16

<210> SEQ ID NO 26
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Primer Vcarp6

<400> SEQUENCE: 26
gcgacggcgc ctacgggttt                                                   20

<210> SEQ ID NO 27
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: Vcarp7

<400> SEQUENCE: 27
ccgggcgagg gatttctctt                                                   20

<210> SEQ ID NO 28
<211> LENGTH: 19
<212> TYPE: DNA
<213> ORGANISM: artificial sequence
<220> FEATURE:
<221> NAME/KEY: misc_feature
<222> LOCATION: (1)..(19)
<223> OTHER INFORMATION: Primer JB677.1

<400> SEQUENCE: 28
gcgggcaggg gaagcctct                                                    19
```

```
<210> SEQ ID NO 29
<211> LENGTH: 21
<212> TYPE: DNA
<213> ORGANISM: artificial sequence
<220> FEATURE:
<221> NAME/KEY: misc_feature
<222> LOCATION: (1)..(21)
<223> OTHER INFORMATION: Primer JB677.2

<400> SEQUENCE: 29
cggcgggcag gggaagcctc t                                              21

<210> SEQ ID NO 30
<211> LENGTH: 22
<212> TYPE: DNA
<213> ORGANISM: artificial sequence
<220> FEATURE:
<221> NAME/KEY: misc_feature
<222> LOCATION: (1)..(22)
<223> OTHER INFORMATION: Primer JB677.3

<400> SEQUENCE: 30
gttgcttcgg cgggcagggg aa                                             22
```

DETECTION OF FUNGAL PATHOGENS USING THE POLYMERASE CHAIN REACTION

This is a divisional of U.S. patent application Ser. No. 09/939,379, filed Aug. 24, 2001 now U.S. Pat. No. 6,645,720 which claims the benefit of U.S. Provisional Application No. 60/274,540, filed Mar. 9, 2001.

FIELD OF THE INVENTION

The present invention relates to the use of primers in polymerase chain reaction assays for the detection of stone fruit and nut, in particular almond pathogens *Colletotrichum acutatum, Alternaria* spp., and *Cladosporium carpophilum*. The use of these primers enables the detection of specific isolates of fungal pathogens and the monitoring of disease development in plant populations. The present-invention also relates to novel extraction buffer solutions, methods of extracting DNA from tissue, and methods of performing PCR analysis on DNA extracted from tissue.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; *Proc. 1981 Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), *Botrytis* (to benomyl), *Pyrenophora* (to organomercury), *Pseudocercosporella* (to MBC-type fungicides) and *Mycosphaerella fijiensis* to triazoles to mention just a few (Jones and Clifford; Cereal Diseases, John Wiley, 1983).

Commercial almond growers are faced with a number of fungi that infect their crops in diverse ways. The impact of these pathogens on tree growth depends on a number of factors, and the cause is not immediately apparent from the symptoms a diseased tree may present. Vascular pathogens invade and plug the xylem vessels, thereby halting movement of water and nutrients up from roots (Integrated Pest Management for Almonds, U. California Division of Agriculture and Natural resources publication 3308 (1985)). Symptoms often reflect a partial or complete cut-off from food or water as vascular tissues are closed. Thus, symptoms of crown and root rots of almond, as well as wilts caused by pathogens infecting leaf and branch tissues, may appear very similar to one another; and similar to the consequences of environmental conditions such as the availability of nutrients and water and factors affecting their uptake.

Some pathogens cause infections that are limited to branches, foliage, and fruit. Several of the fungi and bacteria that cause disease in almonds have been found to infect orchards during the fall months and over-winter in host tissues. During the spring, they produce localized lesions or larger infections that become evident after environmental conditions such as a recent rain or irrigation promote the growth of the pathogens.

The same pathogens that cause economic problems in almond orchard management also affect other crops. For instance, *Cladosporium carpophilum* has a host range that extends over stone fruits. For example, in addition to the scabs it causes in almond crops, *C. carpophilum* also causes scabs in peaches, nectarines, apricots, plums, and cherries (*Compendium of Stone Fruit Diseases*, Ogawa, J. M.; Zehr, E. I.; Bird, G. W.; Ritchie, D. F.; Uriu, K.; Uyemoto, J. K. eds., p. 11 (1995 APS Press, St. Paul, Minn.)).

*Alternaria* spp. has been documented as causing infection on many economically important crops. To date, it has been reported to cause alternaria blight of peas, and alternaria leaf spots have been reported on peanuts, almonds, corn, cotton, and in all soybean growing areas of the world (*Compendium of Soybean Diseases*, 4th Ed. Hartman, G. L.; Sinclair, J. B.; Rupe, J. C. eds., pp. 12–13 (1999, APS Press, St. Paul, Minn.)); (*Compendium of Cotton Diseases*, Watkins, G. M. ed., p. 28 (1981, APS Press, St. Paul, Minn.); *Compendium of Pea Diseases*, Hagedorn, D. J., ed., p. 15 (1984, APS Press, St. Paul, Minn.)); (*Compendium of Peanut Diseases*, Porter, D. M.; Smith, D. H.; Rodriguez-Kabana, R. eds. Pp. 13 (1984, APS Press, St. Paul, Minn.); (*Compendium of Stone Fruit Diseases*, Ogawa, J. M.; Zehr, E. I.; Bird, G. W.; Ritchie, D. F.; Uriu, K.; Uyemoto, J. K. eds.,p. 11 (1995 APS Press, St. Paul, Minn.)); and *Compendium of Corn Diseases*, 3rd Ed. White, D. G., ed., p. 25 (1999, APS Press, St. Paul, Minn.)). *Alternaria* spp. is responsible for widespread leaf and pod spots on beans grown in Brazil, Cananda, Costa Rica, Colombia, Chile, East Africa, England, Mexico, the United States, and Venezuela (*Compendium of Bean Diseases*, Hall, R. ed., p. 14 (1991, APS Press, St. Paul, Minn.)). *Alternaria* spp. also form lesions on potatoes and the leaves of other solanaceous crops; (*Compendium of Potato Diseases*, Hooker, W. J. ed., p. 44 (1981, APS Press, St. Paul, Minn.)) and appear as secondary infections on sugar beet leaves (*Compendium of Beet Diseases and Insects*, Whitney, E. D., Duffus, J. E. eds., p. 11 (1991 APS Press, St. Paul, Minn.)). It causes grain molds in sorghum (*Compendium of Sorghum Diseases*, Frederiksen, R. A. ed., p. 36 (1986 APS Press, St. Paul, Minn.)) and is one cause of black mold rot of tomato (*Compendium of Tomato Diseases*, Jones, J. B.; Jones, J. P.; Stall, R. E.; Zitter, T. A., eds., p. 46 (1991 APS Press, St. Paul, Minn.)). *Alternaria* spp. also causes fruit spot of papaya, a major disease in orchards located in dry areas and in mangos (*Compendium of Tropical Fruit Diseases*, Ploetz, R. C.; Zentmyer, G. A.; Nishijima, W. T.; Rohrbach, K. G.; Ohr, H. D., eds., pp. 34 and 58 (1994 APS Press, St. Paul, Minn.)).

*Colletotrichum acutatum* has been reported to infect a large number of fruit crops including avocado, strawberry, almond, apple, and peach. *C. acutatum* causes post-harvest fruit diseases in avocado and mango. *C. acutatum* is also known to cause both post-bloom fruit drop and key lime anthracnose in citrus crops (see Freeman, S. et al. ,1998, *Plant Disease* Vol. 82, No. 6, pp. 596–605).

In view of the above, there is a real need for the development of technology that will allow the identification of specific races of pathogenic fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

In a preferred embodiment, the invention provides ITS-derived diagnostic primers for the detection of *Colletotrichum acutatum*, *Alternaria* spp., and *Cladosporium carpophilum*.

This invention provides the possibility of assessing potential damage in a specific crop variety/pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of *Colletotrichum acutatum*, *Alternaria* spp., and *Cladosporium carpophilum*.

The invention also provides methods for preparing an extract of DNA from tissue using novel DNA extraction buffer. The invention further provides for methods for performing PCR analysis on DNA extracted from tissue using the novel DNA extraction buffer and methods of preparing an extract of DNA.

BRIEF DESCRIPTION OF THE SEQUENCES IN THE SEQUENCE LISTING

SEQ-ID-NO: 1 Oligonucleotide Primer ITS1
SEQ-ID-NO: 2 Oligonucleotide Primer ITS2
SEQ-ID-NO: 3 Oligonucleotide Primer ITS3
SEQ-ID-NO: 4 Oligonucleotide Primer ITS4
SEQ-ID-NO: 5 Oligonucleotide Primer FORWARD
SEQ-ID-NO: 6 Oligonucleotide Primer REVERSE
SEQ-ID-NO: 7 Oligonucleotide Primer CaINT-1
SEQ-ID-NO: 8 Oligonucleotide Primer CaINT-2
SEQ-ID-NO: 9 Oligonucleotide Primer CaInt2
SEQ-ID-NO: 10 Oligonucleotide Primer JB677
SEQ-ID-NO: 11 Oligonucleotide Primer JB678
SEQ-ID-NO: 12 Oligonucleotide Primer JB679
SEQ-ID-NO: 13 Oligonucleotide Primer Alal-1
SEQ-ID-NO: 14 Oligonucleotide Primer Alal-2
SEQ-ID-NO: 15 Oligonucleotide Primer Alal-3
SEQ-ID-NO: 16 Oligonucleotide Primer Alal-4
SEQ-ID-NO: 17 Oligonucleotide Primer Alal-5
SEQ-ID-NO: 18 Oligonucleotide Primer Alal-6
SEQ-ID-NO: 19 Oligonucleotide Primer Alt1
SEQ-ID-NO: 20 Oligonucleotide Primer Alt2
SEQ-ID-NO: 21 Oligonucleotide Primer Vcarp1
SEQ-ID-NO: 22 Oligonucleotide Primer Vcarp2
SEQ-ID-NO: 23 Oligonucleotide Primer Vcarp3
SEQ-ID-NO: 24 Oligonucleotide Primer Vcarp4
SEQ-ID-NO: 25 Oligonucleotide Primer Vcarp5
SEQ-ID-NO: 26 Oligonucleotide Primer Vcarp6
SEQ-ID-NO: 27 Oligonucleotide Primer Vcarp7
SEQ-ID-NO: 28 Oligonucleotide Primer JB677.1
SEQ-ID-NO: 29 Oligonucleotide Primer JB677.2
SEQ-ID-NO: 30 Oligonucleotide Primer JB677.3

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. ITS DNA sequences from different pathotypes within a pathogen species or-genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers were able to distinguish numerous races of *Gremmeniella abietina*, the causal agent of scleroderris canker in conifers. U.S. Pat. No. 5,585,238.(herein incorporated by reference in its entirety) describes primers derived from the ITS sequences of the ribosomal RNA gene region of strains of *Septoria, Pseudocercosporella*, and *Mycosphaerella* and their use in the identification of these fungal isolates using PCR-based techniques. In addition, U.S. Pat. No. 5,955,274 (herein incorporated by reference in its entirety) describes primers derived from the ITS sequences of the ribosomal RNA gene region of strains of *Fusarium* and their use in the identification of these fungal isolates using PCR-based techniques. Furthermore, U.S. Pat. No. 5,800,997 (herein incorporated by reference in its entirety) describes primers derived from the ITS sequences of the ribosomal RNA gene region of strains of *Cercospora, Helminthosporium, Kabatiella*, and *Puccinia* and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Sequences of representative oligonucleotide primers derived from ITS sequences are disclosed in SEQ-ID-NOs: 1–4 and 7–30. The sequences find use in the PCR-based identification of the pathogens of interest. In a preferred embodiment, the primer comprises a nucleotide sequence of SEQ ID NOS: 10–30.

The present invention also provides pairs of oligonucleotide primers. In one embodiment, the pair comprises or consists of at least one primer of SEQ ID NO:1–4 or 7–30. In a preferred embodiment, the pair consists of at least one primer of SEQ ID NO:10–30.

In yet other embodiments, a pair of oligonucleotide primers, is selected from the group consisting of: SEQ ID NO:30 and SEQ ID NO:4; SEQ ID NO:27 and SEQ ID NO:4; SEQ ID NO:16 and SEQ ID NO:12; SEQ ID NO:16 and SEQ ID NO:18; SEQ ID NO:17 and SEQ ID NO:12; SEQ ID NO:1 and SEQ ID NO:27; SEQ ID NO:24 and SEQ ID NO:25; and SEQ ID NO:21 and SEQ ID NO:4.

In preferred embodiments, the pair of oligonucleotide primers consists of SEQ ID NO:16 and SEQ ID NO:12; or SEQ ID NO:16 and 18; or SEQ ID NO:17 and SEQ ID NO:12; or SEQ ID NO:24 and SEQ ID NO:25.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991; *Physiol. and Molec. Plant Pathol.* 39: 1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674), who used similar techniques to distinguish the banana pathogens *Mycosphaerella fijiensis* and *Mycospharella musicola*.

The target DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287. The ITS rDNA sequences are compared within each pathogen group to locate divergences that might be useful to test in PCR to distinguish the different species and/or strains. From the identification of divergences, numerous primers are synthesized and tested in PCR-amplification. Templates used for PCR-amplification testing are firstly purified pathogen DNA, and subsequently DNA isolated from infected host plant tissue. Thus, it is possible to identify pairs of primers that are diagnostic, i.e. that identify one particular pathogen species or strain but not another species or strain of the same pathogen. Primers are also designed to regions highly conserved among the species to develop genus-specific primers as well as primers that will identify any of several fungal pathogens that cause a particular disease. For example, primers are developed to differentiate *Colletotrichum acutatum*, *Alternaria* spp., and *Cladosporium carpophilum*.

Preferred primer combinations are able to distinguish between the different species or strains in infected host tissue, i.e. host tissue that is infected with a specific pathogen genus, species or strain. This invention provides numerous primer combinations that distinguish *Colletotrichum acutatum*, *Alternaria* spp., and *Cladosporium carpophilum*. The primers of the invention are designed based on sequence differences among the ITS rDNA regions. A minimum of one base pair difference between sequences can permit design of a discriminatory primer. Primers designed to a specific fungal DNA sequence can be used in combination with a primer made to a conserved sequence region flanking the region containing divergences to amplify species-specific PCR fragments. In general, primers should have a theoretical melting temperature between about 60 to about 70 degree ° C. to achieve good sensitivity and should be void of significant secondary structure and 3' overlaps between primer combinations. In preferred embodiments, primers are anywhere from approximately 5–30 nucleotide bases long.

The present invention provides, a method for the detection of a fungal pathogen, comprising the steps of:
  (a) isolating DNA from a plant tissue infected with a pathogen;
  (b) subjecting said DNA to polymerase chain reaction amplification using at least one primer according to SEQ ID NO:1–4 and 7–30; and
  (c) detecting said fungal pathogen by visualizing the product or products of said polymerase chain reaction amplification.

In a preferred embodiment, the primer is at least one according to SEQ ID NO:10–30.

In another embodiment, the method for detection is used when the fungal pathogen is *Colletotrichum acutatum*, *Alternaria* spp., and *Cladosporium carpophilum*.

In another embodiment, the invention provides a method for the detection of a fungal pathogen, comprising the steps of:
  (a) isolating DNA from a plant tissue infected with said fungal pathogen;
  (b) amplifying a part of the Internal Transcribed Spacer sequence of said fungal pathogen using said DNA as a template in a polymerase chain reaction with a pair of primers wherein the pair comprises or consists of at least one primer of SEQ ID NO:1–4 or 7–10. In a preferred embodiment, the pair consists of at least one primer of SEQ ID NO:10–30; and
  (c) detecting said fungal pathogen by visualizing the amplified part of the Internal Transcribed Spacer sequence.

In a preferred embodiment, the method detects a fungal pathogen, wherein said fungal pathogen is *Colletotrichum acutatum, Alternaria* spp., and *Cladosporium carpophilum*.

In yet other embodiments, the method of detection uses a pair of primers, wherein said pair of primers is selected from the group consisting of: SEQ ID NO: 30 and SEQ ID NO:4; SEQ ID NO:27 and SEQ ID NO:4; SEQ ID NO:16 and SEQ ID NO:12; SEQ ID NO:16 and SEQ ID NO:18; SEQ ID NO:17 and SEQ ID NO:12; SEQ ID NO:1 and SEQ ID NO:27; SEQ ID NO:24 and SEQ ID NO:25; and SEQ ID NO:21 and SEQ ID NO:4.

In preferred embodiments, the pair of oligonucleotide primers consists of SEQ ID NO:16 and SEQ ID NO:12; or SEQ ID NO:16 and 18; or SEQ ID NO:17 and SEQ ID NO:12; or SEQ ID NO:24 and SEQ ID NO:25.

The present invention also provides a method for performing PCR analysis on DNA extracted from tissue, comprising the steps of:
(a) taking a plurality of random tissue samples from an organism population;
(b) adding the extraction buffer described in Example 2, to the tissue samples;
(c) macerating the tissue samples and extraction buffer to form an extract;
(d) removing the extract from the macerated tissue and buffer; and
(e) performing PCR analysis on the extract.

In another embodiment, the method further comprises the step of boiling the extract after removing it from the macerated tissue and buffer.

In yet another embodiment, the method further comprises the step of diluting the extract.

In a preferred embodiment, the method uses an organism population that is a plant population. In more preferred embodiments, the method uses tissue samples selected from leaves, stems, roots, blossoms, immature flowers, peduncles, hulls, fruits, immature fruits, or woody tissue.

In another preferred embodiment, the method uses the extraction buffer comprising: 100 mM Tris, pH 8.0; 1.4 M NaCl; 20 mM EDTA; 2% w/v CTAB; 2% w/v PVP and 0.1% w/v ascorbic acid.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

In an embodiment of the invention, the diagnostic kit used in detecting a fungal pathogen, comprises a primer of the present invention as described above.

In yet another embodiment, the diagnostic kit used in detecting a fungal pathogen, comprises a pair of primers of the present invention as described above. The primers, methods and kits of the present invention are useful for detecting the presence of fungal pathogens in any plants or plant parts that are infected by fungal pathogens. In particular, the present invention is useful for detection of *Colletotrichum acutatum, Alternaria* spp., and *Cladosporium carpophilum*. Examples of plants or plant tissues or plant parts infected by these pathogens include, but are not limited to, stone fruits, nuts, solanaceous plants such as tomato and potato, peanuts, corn, sorghum, peas, papaya, avacado, apples, and sugarbeets. Examples of stone fruits include, but are not limited to peaches, nectarines, cherries, apricots and plums. Examples of nut crops include, but are not limited to peanuts, almonds, walnuts, cashews, hazelnuts, brazil nuts, etc.

The examples below show typical experimental protocols that can be used in the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Fungal Isolates and Genomic Fungal DNA Extraction

See Table 1 for a listing of the fungal isolates used and their source. Fungi are grown on PDA (Potato Dextrose Agar) plates. Cultures are incubated for up to 10 days at 28° C. Mycelia are ground in liquid nitrogen, and total genomic DNA is extracted using the protocol of Lee and Taylor (1990; In: *PCR Protocols: A Guide to Methods and Applications*; Eds.: Innes et al.; pages 282–287).

TABLE 1

Source of Test Isolates

| Isolate | | Source | Isolation | Geographic Origin |
|---|---|---|---|---|
| *Colletotrichum acutatum* | 26255 | ATCC[1] | Tomato | New Zealand |
| *Colletotrichum acutatum* | 42373 | ATCC[1] | Mango | Australia |
| *Colletotrichum acutatum* | 60468 | ATCC[1] | *Vaccinium corymbosum* | New Zealand |
| *Colletotrichum acutatum* | 66367 | ATCC[1] | Strawberry | Indiana, USA |

TABLE 1-continued

Source of Test Isolates

| | Isolate | Source | Isolation | Geographic Origin |
|---|---|---|---|---|
| *Colletotrichum acutatum* f.sp. pinea | 38689 | ATCC[1] | *Pinus radiata* | — |
| *Colletotrichum gloeosporioides* | 44228 | ATCC[1] | *Stylosanthes hamata* cv. Verano | Australia |
| *Colletotrichum gloeosporioides* | 38237 | ATCC[1] | Mango | — |
| *Cladosporium carpophilum* | 52935 | ATCC[1] | Peach | Georgia, USA |
| *Cladosporium carpophilum* | BS-1 | Jones[2] | Peach | Michigan, USA |
| *Cladosporium carpophilum* | BS-2 | Jones[2] | Peach | Michigan, USA |
| *Cladosporium carpophilum* | BS-3 | Jones[2] | Peach | Michigan, USA |
| *Cladosporium carpophilum* | BS-4 | Jones[2] | Peach | Michigan, USA |
| *Cladosporium carpophilum* | BS-5 | Jones[2] | Peach | Michigan, USA |
| *Cladosporium carpophilum* | BS-6 | Jones[2] | Peach | Michigan, USA |
| *Alternaria alternata* | 56835 | ATCC[1] | Wheat grain | England |
| *Alternaria alternata* | 34509 | ATCC[1] | Apple | Japan |
| *Alternaria alternata* | 26294 | ATCC[1] | Tobacco | Maryland, USA |
| *Alternaria alternata* f.sp. *lycopersici* | 60647 | ATCC[1] | Tomato | Greece |
| *Alternaria alternata sensu lato* | Aa001 | Pryor[3] | Almond | — |
| *Alternaria alternata sensu lato* | Aa002 | Pryor[3] | Almond | — |
| *Alternaria alternata sensu lato* | Aa003 | Pryor[3] | Almond | — |
| *Alternaria alternata sensu lato* | Aa004 | Pryor[3] | Almond | — |
| *Alternaria alternata sensu lato* | Aa005 | Pryor[3] | Almond | — |
| *Alternaria alternata sensu lato* | Aa006 | Pryor[3] | Almond | — |
| *Alternaria sp.* | 2000#47 | Novartis[4] | Almond | California, USA |
| *Alternaria brassicae* | 21-61-02 | Pryor[3] | — | — |
| *Alternaria brassicola* | 2232 | Pryor[3] | — | — |
| *Alternaria radicina* | 96831 | Pryor[3] | — | — |
| *Alternaria petroselini* | 06-196 | Pryor[3] | — | — |
| *Alternaria dauci* | 36613 | Pryor[3] | — | — |
| *Alternaria porri* | 58175 | Pryor[3] | — | — |
| *Alternaria alternata* | P154 | Pryor[3] | Pistachio | — |
| *Alternaria tenuissima* | P59 | Pryor[3] | Pistachio | — |
| *Alternaria arborescens* | P67 | Pryor[3] | Pistachio | — |
| *Alternaria infectoria* | P60 | Pryor[3] | Pistachio | — |
| *Alternaria tenuissima* | 34-015 | Pryor[3] | — | — |
| *Alternaria arborescens* | 39-128 | Pryor[3] | — | — |
| *Alternaria infectoria* | 27-193 | Pryor[3] | — | — |
| *Colletotrichum fragariae* | 26010 | ATCC[1] | Bean | Florida, USA |
| *Colletotrichum fragariae* | 58718 | ATCC[1] | Strawberry | Florida, USA |
| *Monilinia laxa* | 32671 | ATCC[1] | Nectarine | California, USA |
| *Monilinia fructicola* | 32670 | ATCC[1] | Peach | California, USA |
| *Whetzelinia sclerotiorum* | 46762 | ATCC[1] | Cauliflower | Australia |
| Unknown | 2000#69A1 | Novartis[4] | Almond | California, USA |
| Unknown | 2000#105C | Novartis[4] | Almond | California, USA |
| Unknown | 2000#106A(2P) | Novartis[4] | Almond | California, USA |

[1]American Type Culture Collection; Rockville, MD, USA
[2]Jones, A.L.; Michigan State University, East Lansing, MI, USA (Strains documented in Phytopathology (1999) 89: 100–108)
[3]Pryor, B.; University of California, Davis, CA, USA
[4]Novartis Agribusiness Biotechnology Research, Inc.; Research Triangle Park, NC, USA Example 2

DNA Extraction from Almond Tissues

DNA was extracted from almond leaves by using a bulk maceration method with a modified version of the CTAB extraction buffer (Wang et al., 1993, "PCR amplification from single seeds, facilitating DNA marker-assisted breeding," Nucleic Acids Res. 21:2527). The bulk maceration method was used to isolate DNA from several naturally infected tissues from the field. The potential concentration ranges of the buffer ingredients of the modified CTAB extraction buffer are as follows:

approximately 100 mM Tris, pH 8.0;
0.2–2.0 M NaCl;
1–200 mM ethylenediaminetetraacetic acid (EDTA);
0.1–5% w/v hexadecyltrimethylammonium (CTAB);
0.1–5% w/v polyvinylpyrolidine (PVP); and
0.01–2% w/v ascorbic acid.

In other embodiments of the invention, the DNA extraction buffer comprises 100 mM Tris, pH 8.0; or comprises 1.4

M NaCl; or comprises 20 mM EDTA; or comprises 2% w/v CTAB; or comprises 2% w/v PVP; or comprises 0.1% w/v ascorbic acid.

However, in the preferred embodiment of the bulk maceration method, the following concentrations are used: 100 mM Tris, pH 8.0; 1.4 M NaCl; 20 mM EDTA; 2% w/v CTAB; 2% w/v PVP and 0.1% w/v ascorbic acid.

The present invention provides a method for preparing an extract of DNA from tissue, comprising the steps of:
(a) taking a plurality of random tissue samples from an organism population;
(b) adding the DNA extraction buffer described above, to the tissue samples;
(c) macerating the tissue samples and extraction buffer to form an extract; and
(d) removing the extract from the macerated tissue and buffer.

In another embodiment, the method of extraction takes tissue samples from a plant population. In yet another embodiment, the tissue samples are selected from leaves, stems, roots, blossoms, immature flowers, peduncles, hulls, fruits, immature fruits, or woody tissue.

In a preferred embodiment the method of extraction uses the extraction buffer comprising: 100 mM Tris, pH 8.0; 1.4 M NaCl; 20 mM EDTA; 2% w/v CTAB; 2% w/v PVP and 0.1% w/v ascorbic acid.

DNA is extracted from almond tissues as follows:

Bulk Maceration Method:

(1) A sample consists of almond tissue taken from trees suspected of disease within a given orchard.
(2) Samples are handled individually using a different pair of gloves for each. Any implements used in preparing the samples are washed with water and then with 70% EtOH between each sample.
(3) Samples are separated into subsamples for testing according to tissue:
  A. Blossoms, immature flowers, and peduncles.
  B. Hulls from last season's almonds (mummies) and old crescents (immature fruit). Only the outer part of the almond fruit that was once fleshy and can now be separated from the shell of the nut is to be tested.
  C. Hulls from fresh almonds and crescents from this season. Again, only the outer, fleshy part of the fruit is tested.
  D. Woody tissue.
(4) The sample is placed in a Bioreba (Reinach, Switzerland) heavy duty plastic bag (cat#490100). The plant tissue is weighed, plastic bag with leaves minus the tare (weight of the plastic bag).
(5) A volume (mL) of well-mixed CTAB extraction buffer is added per gram fresh weight of sample according to the following:

| Tissue | Volume/Weight |
|---|---|
| A. Blossoms, peduncles | 3 X |
| B. Hulls, old almond fruit | 4 X |
| C. Hulls, fresh almond fruit | 2 X |
| D. Woody tissue | 2 X |

CTAB extraction buffer: (100 mM Tris, pH 8.0; 1.4 M NaCl; 20 mM ethylenediaminetetraacetic acid (EDTA); 2% w/v hexadecyltrimethylammonium bromide (CTAB); 2% w/v polyvinylpyrolidine (PVP); and 0.1% w/v ascorbic acid. The tissue is macerated using a Bioreba Homex 6 homogenizer (Reinach, Switzerland, cat #400005) set at 90. The sample is ground until tissues appear as broken as possible to liberate fungal DNA.

(6) Once maceration is complete, the extraction is pressed into the bottom of the extraction bag. Using clean scissors cut the bag at a length to allow a 10 or 25 mL transfer pipet to reach the extraction without contaminating the pipettor.
(7) By pipetting up and down several times, the extraction juice is homogenized.
(8) One milliliter of extraction juice is transferred into each of two eppendorf tubes. One of these tubes is immediately frozen in storage for reference. The other is further processed.
(9) The test aliquot is boiled for five minutes. A centrifuge cap sleeve is used to ensure that the tube will not pop open.
(10) The boiled extracted is allowed to cool on ice for 2 minutes.
(11) The extraction is centrifuged at 15,000×G for 5 minutes.
(12) Extracts are either diluted and tested directly (13A) or nucleic acids are purified from them prior to testing (13B).
(13A). Extracts are diluted for testing. Extraction supernatant is added to ice-cold water according to the following scheme:

| Tissue | mL CTAB/g tissue | Dilution Tested |
|---|---|---|
| E. Blossoms, peduncles | 3 X | 1:67 |
| F. Hulls, old almond fruit | 4 X | 1:50 |
| G. Hulls, fresh almond fruit | 2 X | 1:100 |
| H. Woody tissue | 2 X | 1:100 |

(13B) Nucleic acids are purified from almond extracts by performing an equal volume 25:24:1 phenol:chloroform:isoamyl alcohol extraction on 1 mL of homogenized extraction juice. The aqueous phase of this extraction is transferred to a fresh microcentrifuge tube and 0.5 volumes of ice-cold isopropanol are added. After incubation for 20 minutes at −20° C., the precipitate is spun down at 15,000 rpm for 10 minutes. The supernatant is discarded and the pellet is washed with 0.7 mL of 70% ethanol. The wash is discarded and the pellet allowed to dry. The pellet is resuspended in Tris EDTA buffer (10 mM Tris base, 1 mM EDTA, pH 8.0) with RNase added at a concentration of 10 mg/mL. The DNA concentration can be read on a spectrophotometer and adjusted to 100 ng/μL by addition of TE buffer.

TABLE 2

Source of almond tissues used

| Sample Identification | Tissue type | Origin (City, California, USA) |
| --- | --- | --- |
| 1999#3 | Almond hulls | Escalon |
| 1999#5 | Almond hulls | — |
| 1999#11 | Almond hulls | Modesto |
| 1999#41 | Almond hulls | Chico |
| 1999#42 | Almond hulls | Chico |
| 1999#104 | Almond hulls | Salida |
| 1999#109B | Almond hulls | Modesto |
| 1999#118D | Almond hulls | Turlock |
| 2000#8 | Almond hulls | Ripon |
| 2000#11 | Almond hulls | Turlock |
| 2000#19 | Almond hulls | Hughson |
| 2000#31A | Mummified fruit | Ripon |
| 2000#JA-1A | Flower blossoms | — |
| 2000#59B | Flower blossoms and crescents | Gridley |

Example 3

Polymerase Chain Reaction Amplification

Polymerase chain reactions are performed with the GeneAmp Kit from Perkin-Elmer (Foster City, Calif.; part no. N808-0009) using 50 mM KCl, 2.5 mM $MgCl_2$, 10 mM Tris-HCl, pH8.3, containing 200 μM of each dTTP, dATP, dCTP, and dGTP in either 25 or 50 μL reactions containing 50 μM each primer, 0.25 U/μL of Taq polymerase and 0.2 ng/μL of genomic DNA. Reactions are run for 30–40 cycles of 15 s at 94° C., 15 s at 50° C.–70° C., and 45 s at 72° C. in a Perkin-Elmer Model 9600 or 9700 thermal cycler. The products are analyzed by loading 10 μl of each PCR sample on a 1.0% agarose gel and electrophoresing.

Example 4

Synthesis and Purification of Oligonucleotides

Oligonucleotides (primers) are synthesized by, for example, either Integrated DNA Technologies (Coralville, Iowa) or Midland Certified Reagent Company (Midland, Tex.).

Example 5

Cloning and Sequencing of ITS Region rDNA

ITS region sequences are PCR-amplified using conserved primers ITS1 and ITS4 (SEQ-ID-NO: 1 and 4) as described in Example 3. Products cloned into the pCR®2.1-TOPO TA-cloning vector using the TOPO-TA Cloning Kit (Invitrogen, Carlsbad, Calif.; part no. K4550-40) according to manufacturer's directions. Clones containing the ITS fragment inserts are sequenced using the TA cloning vector's FORWARD (5'-gtaaaacgacggccagt-3'; SEQ ID NO:5) and REVERSE (5'-caggaaacagctatgac-3'; SEQ ID NO:6) primers. Sequencing is performed on an ABI PRISM 377™ DNA sequencer (Perkin Elmer Applied Biosystems, Foster City, Calif.).

Example 6

Design of Species-specific PCR Primers

Example 6 is broken down into three subsections describing details of the design of specific primers for *Colletotrichum acutatum*, *Alternaria* spp., and *Cladosporium carpophilum*. A few common steps are involved in the design of primers for the three target species. In the design of each assay, Internal Transcribed Spacer region DNA sequences are obtained either from the GenBank database of the National Center for Biotechnology Information (www.ncbi.nlm.nih.gov) or from PCR-amplified and sequenced DNA from isolates in Example 1 according to the protocol in Example 5. A multiple sequence alignment is made of these sequences. The alignment is analyzed for divergences among the target sequences and among sequences for other fungal DNAs. The divergences permit the development of primers that will specifically amplify target sequences in PCR reactions. Oligonucleotide primers are designed to target regions that contain the greatest differences in sequence among the species analyzed (See individual tables 4–7). These primers are synthesized according to Example 4. In addition, the published ribosomal gene-specific primers ITS1, ITS2, ITS3 and ITS4 (White et al., 1990;In: PCR Protocols; Eds.: Innes et al. pages 315–322) are synthesized for testing in combination with the primers specific for the ITS regions. The conserved fungal ITS region primers are shown in Table 3.

TABLE 3

Conserved primers designed for amplification of fungal ITS region DNA

| Name | Oligo Sequence (5'→3') | Target | Identifier |
| --- | --- | --- | --- |
| ITS1 | TCCGTAGGTGAACCTGCGG | Fungal Nuclear rDNA ITS region | SEQ-ID-NO:1 |
| ITS2 | GCTGCGTTCTTCATCGATGC | Fungal Nuclear rDNA ITS region | SEQ-ID-NO:2 |

TABLE 3-continued

Conserved primers designed for amplification of fungal ITS region DNA

| Name | Oligo Sequence (5'→3') | Target | Identifier |
|---|---|---|---|
| ITS3 | GCATCGATGAAGAACGCAGC | Fungal Nuclear rDNA ITS region | SEQ-ID-NO:3 |
| ITS4 | TCCTCCGCTTATTGATATGC | Fungal Nuclear rDNA ITS region | SEQ-ID-NO:4 |

Example 6A

Design of *Colletotrichum acutatum*-specific PCR Primers

Primers are designed for the specific detection of *Colletotrichum acutatum*. Internal Transcribed Spacer region I DNA sequences for *C. acutatum* are obtained from the GenBank database. Those sequences include accession numbers Z32907, Z32913, Z32915, Z32916, Z32917, Z32918, Z32921, Z32922, Z32924, Z32925, Z32926, and Z32928. A multiple sequence alignment is made of these sequences along with ITS I region sequences for other almond pathogens (Z32930 for *Colletotrichum coccodes*; Z32938, *C.dematium*; Z32943, *C.fragariae*; Z32961, *C.gloeosporioides*; Z32981, *C.graminicola*; Z32984, *C.linicola*; Z33000, *C.trichellum*). The alignment is analyzed for divergences between the target sequences and sequences for other fungal DNAs. The divergences permit the development of primers that will specifically amplify *C. acutatum* ITS region DNA when used in PCR reactions. Oligonucleotide primers JB677, JB677.1, JB677.2, JB677.3 and JB678 (SEQ-ID-NO: 10, 28, 29, 30 and 11, respectively) are designed to target the ITS region 1 DNA of *C. acutatum*. Primers JB677, JB677.1, JB677.2, and JB677.3 are targeted to the same region of ITS1 and demonstrate how adding or removing bases to a primer that contains a target-specific sequence can produce a diverse number of oligonucleotides for use in the detection of the same target.

SEQ-ID-NO: 7 Oligonucleotide Primer CaINT-1
SEQ-ID-NO: 8 Oligonucleotide Primer CaINT-2
SEQ-ID-NO: 9 Oligonucleotide Primer CaInt2

In a similar alignment obtained from the literature (Bailey et al., Phytopathology 86: 1076–1083), ITS region 2 DNA sequences of several *Colletotrichum* species are compared. The alignment in this report is used to find divergences among the species compared for the design of a *C. acutatum* ITS region 2 primer. Oligonucleotide primer JB679 (SEQ-ID-NO: 12) is designed to target ITS region 2 DNA of *C. acutatum*. The *C. acutatum* specific primers are shown in Table 4. These primers may be used in combination with one another, with one of the conserved primers in Table 3, or with one of the *C. acutatum* specific primers from the literature (Primers CaINT-1, 5'-GGCGCCGGCCCCCAC-CACGGGGA-3' and CaINT-2, 5'- GGCGCCGGCCCCGT-CACGGGGG-3' referenced in Adaskaveg and Hartin, Phytopathology 87:979–987, or primer CaInt2, 5'-GGGGAAGCCTCTCGCGG-3' referenced in Sreenivasaprasad et al. Plant Pathology (1996) 45, 650–655) to target *C. acutatum* DNA.

TABLE 4

Primers designed for detection of *Colletotrichum acutatum*

| Name | Oligonucleotide sequence (5'→3') | Identifier |
|---|---|---|
| JB677 | CGGGCAGGGGAAGCCTC | SEQ-ID-NO:10 |
| JB678 | GGAAGCCTCTCGCGGGC | SEQ-ID-NO:11 |
| JB679 | ATCCCAGTGCGAGACGTTAG | SEQ-ID-NO:12 |
| JB677.1 | GCGGGCAGGGGAAGCCTCT | SEQ-ID-NO:28 |
| JB677.2 | CGGCGGGCAGGGGAAGCCTCT | SEQ-ID-NO:29 |
| JB677.3 | GTTGCTTCGGCGGGCAGGGGAA | SEQ-ID-NO:30 |

Example 6B

Design of *Alternaria* spp.-specific PCR Primers

Primers are designed for the specific detection of *Alternaria*-spp. ITS region DNA sequences for *A. alternata* were obtained as described in Example 5 for four ATCC isolates (56835, 34509, 26294, and 60647) as well as plate isolates obtained from almond sample 2000#47 (See Table 1 for more information on isolates). Additionally, GenBank sequences for the *A. alternata* ITS region were obtained (Accession # AF229461, AF229460, AF229459, AF218791, AJ276059, AJ276055, and AF071346). These sequences were aligned in SeqMan II ver 3.6.0 (DNAStar, Madison, Wis., U.S.A.). A consensus sequence of these sequences was generated and labeled "*Alternaria* ITS sequence".

A multiple sequence alignment is made of this sequence along with ITS region sequences for other almond pathogens. These include sequences obtained from GenBank for *Colletotrichum gloeosporioides* (Accession #AF090855), *C. acutatum* (AF090853), *C. fragariae* (AF090854), *Venturia carpophila* (syn. *Fusicladium carpophilum, Cladosporium carpophilum*) (AF065849), *Monilinia fructigena* (Z73781), *M. laxa* (Z73786), *Sclerotinia sclerotiorum* (Z73799), and *Botrytis cinerea* (Z73765). An ITS region sequence generated as in Example 5 for ATCC *Fusicladium carpophilum* isolate 52935 is also included in the multiple sequence alignment.

The alignment is analyzed for divergences between the *A. alternata* consensus sequence target and other fungal sequences. The divergences found allow for the development of primers that will specifically amplify *Alternaria* spp. ITS region DNA when used in PCR reactions. Oligonucleotide primers Alal-1, Alal-2, Alal-3, Alal-4, alal-5, and Alal-6 (SEQ-ID-NOs: 13–18) are designed to target the ITS region DNA of *Alternaria* spp. (Table 5).

Additionally, these primers can be used with conserved ITS region primers in Table 3 as well as other ITS derived *Alternaria* spp. primers found in the literature (primers alt1, 5'-ATTGCAATCAGCGTCAGTAAC-3' and alt2, 5-CAAG-CAAAGCTTGAGGGTACA-3'Zur et al. 1999. J. Food Protection 62(10) p 1191–1197) (SEQ-ID-NOs: 19 and 20, respectively).

TABLE 5

Primers designed for detection of *Alternaria* spp.

| Name | Oligonucleotide sequence (5'->3') | Identifier |
|---|---|---|
| Alal-1 | AAATATGAAGGCGGGCTGGA | SEQ-ID-NO:13 |
| Alal-2 | AGACCTTTGCTGATAGAGAGTGCGA | SEQ-ID-NO:14 |
| Alal-3 | CCTTTGCTGATAGAGAGTGCGACTT | SEQ-ID-NO:15 |
| Alal-4 | CTCGGGGTTACAGCCTTGCT | SEQ-ID-NO:16 |
| Alal-5 | AACCTCTCGGGGTTACAGCCTTGCT | SEQ-ID-NO:17 |
| Alal-6 | TGATAGAGAGTGCGACTTGT | SEQ-ID-NO:18 |

Example 6C

Design of *Cladosporium carpophilum*-specific PCR Primers

Primers are designed for the specific detection of *Cladosporium carpophilum*. ITS region DNA sequences for *C. carpophilum* were obtained as described in Example 5 for six isolates (BS-1, BS-2, BS-3, BS-4, BS-6, and ATCC isolate 52935). One additional sequence for *C. carpophilum* ITS region DNA was obtained from GenBank (Accession # AF065489). These sequences were aligned in SeqMan II ver 3.6.0 (DNAStar, Madison, Wis., U.S.A.). A consensus sequence of these sequences was generated and labeled "Vcarpophila consensus".

A multiple sequence alignment is made of this sequence along with ITS region sequences for other almond pathogens. These include sequences obtained from GenBank for *Colletotrichum gloeosporioides* (Accession #AF090855), *C. acutatum* (AF090853), *C. fragariae* (AF090854), *Monilinia fructigena* (Z73781), *M. laxa* (Z73786), *Sclerotinia sclerotiorum* (Z73799), and *Botrytis cinerea* (Z73765). The consensus sequence generated in Example 6B for multiple *Alternaria alternata* sequences is also included in the multiple sequence alignment.

The alignment is analyzed for divergences between the *C. carpophilum* consensus sequence target and other fungal sequences. The divergences found allow for the development of primers that will specifically amplify *C. carpophilum* ITS region DNA when used in PCR reactions. Oligonucleotide primers Vcarp1, Vcarp2, Vcarp3, Vcarp4, Vcarp5, Vcarp6, and Vcarp7 (SEQ-ID-NOs: 21–27) are designed to target the ITS region of *C. carpophilum* (Table 6). These primers can be used with conserved ITS region primers in Table 3.

TABLE 6

Primers designed for detection of *Cladosporium carpophilum*

| Name | Oligonucleotide sequence (5'->3') | Identifier |
|---|---|---|
| Vcarp1 | TGCCGGAATCAGCAAGCCCT | SEQ-ID-NO:21 |
| Vcarp2 | CAACCGCGGCCCGGAT | SEQ-ID-NO:22 |
| Vcarp3 | TCAGCAAGCCCTGCCTAGAA | SEQ-ID-NO:23 |
| Vcarp4 | GTCTGAGGAGAAAGCCAAACGA | SEQ-ID-NO:24 |
| Vcarp5 | GCTCCGGGCGAGGGAT | SEQ-ID-NO:25 |
| Vcarp6 | GCGACGGCGCCTACGGGTTT | SEQ-ID-NO:26 |
| Vcarp7 | CCGGGCGAGGGATTTCTCTT | SEQ-ID-NO:27 |

Example 7

Determination of Primer Specificity to Purified Fungal Genomic DNA

PCRs are performed according to Example 3 using different primer combinations (Table 7) in an attempt to amplify single specific fragments. Specific PCR amplification products are produced from primers designed from the nuclear rDNA ITS regions of each fungal species of interest.

In an initial screen for specificity, PCR reaction mixtures are made according to Example 3 for each of the primer combinations in Table 7. These are run against a negative control (no DNA added), a healthy almond tissue control (prepared as in Example 2) to test for background amplification, and 10 ng of fungal DNA for each of the known species listed in Table 1 prepared as described in example 1.

TABLE 7

Possible combinations of PCR primers for the specific amplification of *Colletotrichum acutatum*, *Alternaria* spp., and *Cladosporium carpophilum*.

| Target Pathogen | 5' primer | 3' primer |
|---|---|---|
| *C. acutatum* | CaINT-1 (SEQ-ID-NO: 7) | JB679 (SEQ-ID-NO: 12) |
| *C. acutatum* | CaINT-2 (SEQ-ID-NO: 8) | JB679 (SEQ-ID-NO: 12) |
| *C. acutatum* | CaInt2 (SEQ-ID-NO: 9) | JB679 (SEQ-ID-NO: 12) |
| *C. acutatum* | JB677.1 (SEQ-ID-NO: 28) | JB679 (SEQ-ID-NO: 12) |
| *C. acutatum* | JB677.1 (SEQ-ID-NO: 28) | ITS4 (SEQ-ID-NO: 4) |
| *C. acutatum* | JB677.1 (SEQ-ID-NO: 28) | ITS2 (SEQ-ID-NO: 2) |
| *C. acutatum* | JB677.2 (SEQ-ID-NO: 29) | JB679 (SEQ-ID-NO: 12) |
| *C. acutatum* | JB677.2 (SEQ-ID-NO: 29) | ITS4 (SEQ-ID-NO: 4) |
| *C. acutatum* | JB677.2 (SEQ-ID-NO: 29) | ITS2 (SEQ-ID-NO: 2) |
| *C. acutatum* | JB677.3 (SEQ-ID-NO: 30) | JB679 (SEQ-ID-NO: 12) |
| *C. acutatum* | JB677.3 (SEQ-ID-NO: 30) | ITS4 (SEQ-ID-NO: 4) |
| *C. acutatum* | JB677.3 (SEQ-ID-NO: 30) | ITS2 (SEQ-ID-NO: 2) |
| *C. acutatum* | JB677 (SEQ-ID-NO: 10) | JB679 (SEQ-ID-NO: 12) |
| *C. acutatum* | JB677 (SEQ-ID-NO: 10) | ITS4 (SEQ-ID-NO: 4) |
| *C. acutatum* | JB677 (SEQ-ID-NO: 10) | ITS2 (SEQ-ID-NO: 2) |
| *C. acutatum* | JB678 (SEQ-ID-NO: 11) | JB679 (SEQ-ID-NO: 12) |
| *C. acutatum* | JB678 (SEQ-ID-NO: 11) | ITS4 (SEQ-ID-NO: 4) |
| *C. acutatum* | JB678 (SEQ-ID-NO: 11) | ITS2 (SEQ-ID-NO: 2) |
| *C. acutatum* | ITS1 (SEQ-ID-NO: 1) | JB679 (SEQ-ID-NO: 12) |
| *C. acutatum* | ITS3 (SEQ-ID-NO: 3) | JB679 (SEQ-ID-NO: 12) |
| *Alternaria* spp. | Alal-4 (SEQ-ID-NO: 16) | ITS2 (SEQ-ID-NO: 2) |
| *Alternaria* spp. | Alal-4 (SEQ-ID-NO: 16) | Alt2 (SEQ-ID-NO: 20) |
| *Alternaria* spp. | Alal-4 (SEQ-ID-NO: 16) | Alal-2 (SEQ-ID-NO: 14) |

TABLE 7-continued

Possible combinations of PCR primers for the specific amplification of *Colletotrichum acutatum*, *Alternaria* spp., and *Cladosporium carpophilum*.

| Target Pathogen | 5' primer | 3' primer |
|---|---|---|
| *Alternaria* spp. | AlaI-4 (SEQ-ID-NO: 16) | AlaI-3 (SEQ-ID-NO: 15) |
| *Alternaria* spp. | AlaI-4 (SEQ-ID-NO: 16) | AlaI-6 (SEQ-ID-NO: 18) |
| *Alternaria* spp. | AlaI-5 (SEQ-ID-NO: 17) | ITS4 (SEQ-ID-NO: 4) |
| *Alternaria* spp. | AlaI-5 (SEQ-ID-NO: 17) | ITS2 (SEQ-ID-NO: 2) |
| *Alternaria* spp. | AlaI-5 (SEQ-ID-NO: 17) | Alt2 (SEQ-ID-NO: 20) |
| *Alternaria* spp. | AlaI-5 (SEQ-ID-NO: 17) | AlaI-2 (SEQ-ID-NO: 14) |
| *Alternaria* spp. | AlaI-5 (SEQ-ID-NO: 17) | AlaI-3 (SEQ-ID-NO: 15) |
| *Alternaria* spp. | AlaI-5 (SEQ-ID-NO: 17) | AlaI-6 (SEQ-ID-NO: 18) |
| *Alternaria* spp. | Alt1 (SEQ-ID-NO: 19) | AlaI-2 (SEQ-ID-NO: 14) |
| *Alternaria* spp. | Alt1 (SEQ-ID-NO: 19) | AlaI-3 (SEQ-ID-NO: 15) |
| *Alternaria* spp. | Alt1 (SEQ-ID-NO: 19) | AlaI-6 (SEQ-ID-NO: 18) |
| *Alternaria* spp. | ITS1 (SEQ-ID-NO: 1) | AlaI-2 (SEQ-ID-NO: 14) |
| *Alternaria* spp. | ITS1 (SEQ-ID-NO: 1) | AlaI-3 (SEQ-ID-NO: 15) |
| *Alternaria* spp. | ITS1 (SEQ-ID-NO: 1) | AlaI-6 (SEQ-ID-NO: 18) |
| *Alternaria* spp. | ITS3 (SEQ-ID-NO: 3) | AlaI-2 (SEQ-ID-NO: 14) |
| *Alternaria* spp. | ITS3 (SEQ-ID-NO: 3) | AlaI-3 (SEQ-ID-NO: 15) |
| *Alternaria* spp. | ITS3 (SEQ-ID-NO: 3) | AlaI-6 (SEQ-ID-NO: 18) |
| *C. carpophilum* | Vcarp1 (SEQ-ID-NO: 21) | Vcarp5 (SEQ-ID-NO: 25) |
| *C. carpophilum* | Vcarp1 (SEQ-ID-NO: 21) | Vcarp6 (SEQ-ID-NO: 26) |
| *C. carpophilum* | Vcarp1 (SEQ-ID-NO: 21) | Vcarp7 (SEQ-ID-NO: 27) |
| *C. carpophilum* | Vcarp1 (SEQ-ID-NO: 21) | ITS4 (SEQ-ID-NO: 4) |
| *C. carpophilum* | Vcarp1 (SEQ-ID-NO: 21) | ITS2 (SEQ-ID-NO: 2) |
| *C. carpophilum* | Vcarp2 (SEQ-ID-NO: 22) | Vcarp5 (SEQ-ID-NO: 25) |
| *C. carpophilum* | Vcarp2 (SEQ-ID-NO: 22) | Vcarp6 (SEQ-ID-NO: 26) |
| *C. carpophilum* | Vcarp2 (SEQ-ID-NO: 22) | Vcarp7 (SEQ-ID-NO: 27) |
| *C. carpophilum* | Vcarp2 (SEQ-ID-NO: 22) | ITS4 (SEQ-ID-NO: 4) |
| *C. carpophilum* | Vcarp2 (SEQ-ID-NO: 22) | ITS2 (SEQ-ID-NO: 2) |
| *C. carpophilum* | Vcarp3 (SEQ-ID-NO: 23) | Vcarp5 (SEQ-ID-NO: 25) |
| *C. carpophilum* | Vcarp3 (SEQ-ID-NO: 23) | Vcarp6 (SEQ-ID-NO: 26) |
| *C. carpophilum* | Vcarp3 (SEQ-ID-NO: 23) | Vcarp7 (SEQ-ID-NO: 27) |
| *C. carpophilum* | Vcarp3 (SEQ-ID-NO: 23) | ITS4 (SEQ-ID-NO: 4) |
| *C. carpophilum* | Vcarp3 (SEQ-ID-NO: 23) | ITS2 (SEQ-ID-NO: 2) |
| *C. carpophilum* | Vcarp4 (SEQ-ID-NO: 24) | Vcarp5 (SEQ-ID-NO: 25) |
| *C. carpophilum* | Vcarp4 (SEQ-ID-NO: 24) | Vcarp6 (SEQ-ID-NO: 26) |
| *C. carpophilum* | Vcarp4 (SEQ-ID-NO: 24) | Vcarp7 (SEQ-ID-NO: 27) |
| *C. carpophilum* | Vcarp4 (SEQ-ID-NO: 24) | ITS4 (SEQ-ID-NO: 4) |
| *C. carpophilum* | Vcarp4 (SEQ-ID-NO: 24) | ITS2 (SEQ-ID-NO: 2) |
| *C. carpophilum* | ITS1 (SEQ-ID-NO: 1) | Vcarp5 (SEQ-ID-NO: 25) |
| *C. carpophilum* | ITS1 (SEQ-ID-NO: 1) | Vcarp6 (SEQ-ID-NO: 26) |
| *C. carpophilum* | ITS1 (SEQ-ID-NO: 1) | Vcarp7 (SEQ-ID-NO: 27) |
| *C. carpophilum* | ITS3 (SEQ-ID-NO: 3) | Vcarp5 (SEQ-ID-NO: 25) |
| *C. carpophilum* | ITS3 (SEQ-ID-NO: 3) | Vcarp6 (SEQ-ID-NO: 26) |
| *C. carpophilum* | ITS3 (SEQ-ID-NO: 3) | Vcarp7 (SEQ-ID-NO: 27) |

When visualized on an ethidium bromide stained gel several primer pairs give satisfactory results: good amplification of target DNA from multiple isolates of the target species with all other reactions (negative control, almond background, and other fungal DNAs) free of both specific and nonspecific reaction products. Some give unsatisfactory results including nonspecific amplification, no amplification of target DNA, and amplification of DNAs from fungal species other that the target. The primer pairs that give the good amplification for their specific targets with no cross-amplification are summarized in Table 8.

TABLE 8

PCR primer pairs providing specific and sensitive amplification of target DNA for *Colletotrichum acutatum*, *Alternaria* spp., and *Cladosporium carpophilum* PCR assays.

| Target Pathogen | 5' primer | 3' primer |
|---|---|---|
| *C. acutatum* | JB677.3 (SEQ-ID-NO: 30) | ITS4 (SEQ-ID-NO: 4) |
| *C. acutatum* | JB677 (SEQ-ID-NO: 27) | ITS4 (SEQ-ID-NO: 4) |
| *Alternaria* spp. | AlaI-4 (SEQ-ID-NO: 16) | AlaI-2 (SEQ-ID-NO: 12) |
| *Alternaria* spp. | AlaI-4 (SEQ-ID-NO: 16) | AlaI-6 (SEQ-ID-NO: 18) |
| *Alternaria* spp. | AlaI-5 (SEQ-ID-NO: 17) | AlaI-2 (SEQ-ID-NO: 12) |
| *C. carpophilum* | ITS1 (SEQ-ID-NO: 1) | Vcarp7 (SEQ-ID-NO: 27) |
| *C. carpophilum* | Vcarp4 (SEQ-ID-NO: 24) | Vcarp5 (SEQ-ID-NO: 25) |
| *C. carpophilum* | Vcarp1 (SEQ-ID-NO: 21) | ITS4 (SEQ-ID-NO: 4) |

Example 7

Validation of Almond Pathogen PCR Assays Against a Panel of Almond Tissue DNA Extractions For the primer pairs that give the best amplification of their given targets (JB677.3 with ITS4 for *C. acutatum*, AlaI-4 with AlaI-2 for *Alternaria* spp., and ITS1 with Vcarp7 for *C. carpophilum*), each is run in PCR reactions against a panel of almond tissue extractions prepared as in Example 2 on tissues listed in Table 2. In this experiment, extractions from sample designated as "1999" are diluted and tested directly. Nucleic acids are purified from extractions on samples designated as "2000" and then tested at a 100 ng per reaction concentration. Results are scored as either positive (+) or negative (−) with any product visible being considered a positive and with nonspecifics recorded if present. Results of these tests are shown in Table 9.

TABLE 9

Results of almond pathogen PCR assays against a panel of Almond tissue DNA extractions.

| Sample Identification | Tissue Type | *Colletotrichum acutatum* | *Alternaria* spp. | *Cladosporium carpophilum* |
|---|---|---|---|---|
| 1999#3 | Almond hulls | + | + | − |
| 1999#5 | Almond hulls | + | + | − |
| 1999#11 | Almond hulls | − | + | − |
| 1999#41 | Almond hulls | − | − | − |
| 1999#42 | Almond hulls | − | + | − |
| 1999#104 | Almond hulls | + | + | − |
| 1999#109B | Almond hulls | + | + | − |

TABLE 9-continued

Results of almond pathogen PCR assays against a panel of Almond tissue DNA extractions.

| Sample Identification | Tissue Type | Colletotrichum acutatum | Alternaria spp. | Cladosporium carpophilum |
|---|---|---|---|---|
| 1999#118D | Almond hulls | − | + | − |
| 2000#8 | Almond hulls | + | + | − |
| 2000#19 | Almond hulls | − | − | − |
| 2000#31A | Mummified fruit | − | + | − |
| 2000#JA-1A | Flower blossoms | + | − | − |
| 2000#59B | Flower blossoms and crescents | − | − | − |

For the thirteen isolates tested, the assays detect and differentiate *Colletotrichum acutatum*, *Alternaria* spp., and *Cladosporium carpophilum* in almond extractions. This experiment demonstrates the utility of these primers in directly characterizing almond tissue extractions for the presence of disease.

Example 8

Validation of Almond Pathogen PCR Assays Against a Panel of Unknown Fungal Isolates Collected from Almond Tissues DNAs are extracted from unknown fungal isolates (Table 1, bottom) collected from almond samples by the method in Example 1. These purified DNA extracts are tested using PCR reaction mixtures made according to Example 3 for each of the primer combinations in Table 8. Table 10 shows the utility of these assays in the characterization of purified fungal isolates grown from almond tissues.

TABLE 10

Results of almond pathogen PCR assays against a panel of Unknown fungal isolates from field-grown almonds.

| Sample Identification | Colletotrichum Acutatum | Alternaria spp. | Cladosporium carpophilum |
|---|---|---|---|
| 2000#69A1 | − | + | − |
| 2000#105C | + | − | − |
| 2000#106A(2P) | − | + | − |

All references cited herein are incorporated by reference in their entireties.

Appendix I:

GenBank sequences used in the development of *C.acutatum* primers

Z32907
C.acutatum (4885) DNA for ITS1 (between small sub-unit and 5.8S rRNA genes)
gi|483613|emb|Z32907.1|CAITS1A[483613]

Z32913
C.acutatum (179) DNA for ITS1 (between small sub-unit and 5.8S rRNA genes)
gi|483614|emb|Z32913.1|CAITS1B[483614]

Z32915
C.acutatum (397) DNA for ITS1 (between small sub-unit and 5.8S rRNA genes)
gi|483615|emb|Z32915.1|CAITS1D[483615]

Z32916
C.acutatum (493/BOX88) DNA for ITS1 (between small sub-unit and 5.8S rRNA genes)
gi|483616|emb|Z32916.1|CAITS1E[483616]

Z32917
C.acutatum (495/17729) DNA for ITS1 (between small sub-unit and 5.8S rRNA genes)
gi|483617|emb|Z32917.1|CAITS1F[483617]

Z32918
C.acutatum (534/90.368) DNA for ITS1 (between small sub-unit and 5.8S rRNA genes)
gi|483618|emb|Z32918.1|CAITS1G[483618]

Z32921

C.acutatum (547/90.410) DNA for ITS1 (between small sub-unit and 5.8S rRNA genes)
gi|483621|emb|Z32921.1|CAITS1J[483621]

Z32922

C.acutatum (549) DNA for ITS1 (between small sub-unit and 5.8S rRNA genes)
gi|483622|emb|Z32922.1|CAITS1K[483622]

Z32924

C.acutatum (602/91.326) DNA for ITS1 (between small sub-unit and 5.8S rRNA genes)
gi|483624|emb|Z32924.1|CAITS1M[483624]

Z32925

C.acutatum (615/91.414) DNA for ITS1 (between small sub-unit and 5.8S rRNA genes)
gi|483625|emb|Z32925.1|CAITS1N[483625]

Z32926

C.acutatum (616/91.414) DNA for ITS1 (between small sub-unit and 5.8S rRNA genes)
gi|483626|emb|Z32926.1|CAITS1O[483626]

Z32928

C.acutatum (NI90) DNA for ITS1 (between small sub-unit and 5.8S rRNA genes)
gi|483627|emb|Z32928.1|CAITS1Q[483627]

Z32930

C.coccodes (527.77) DNA for ITS1 (between small sub-unit and 5.8S rRNA genes)
gi|483630|emb|Z32930.1|CCITS1B[483630]

Z32938

C.dematium (288810) DNA for ITS1 (between small sub-unit and 5.8S rRNA genes)
gi|483639|emb|Z32938.1|CDITS1A[483639]

Z32943

C.fragariae (63-1) DNA for ITS1 (between small sub-unit and 5.8S rRNA genes)

gi|483643|emb|Z32943.1|CFITS1B[483643]

Z32961

C.gloeosporioides (561) DNA for ITS1 (between small sub-unit and 5.8S rRNA genes)
gi|483673|emb|Z32961.1|CGITS1Q[483673]

Z32981

C.graminicola (84032) DNA for ITS1 (between small sub-unit and 5.8S rRNA genes)
gi|483657|emb|Z32981.1|CGITS1AM[483657]

Z32984

C.linicola (103844) DNA for ITS1 (between small sub-unit and 5.8S rRNA genes)
gi|483685|emb|Z32984.1|CLITS1A[483685]

Z33000

C.trichellum (180.52) DNA for ITS1 (between small sub-unit and 5.8S rRNA genes)
gi|483713|emb|Z33000.1|CTITS1A[483713]

Appendix II:

GenBank sequences used in the development of *Alternaria* spp. primers

AF229461

Alternaria alternata strain BMP 21-41-10 internal transcribed spacer 1, partial sequence; 5.8S ribosomal RNA gene, complete sequence; and internal transcribed spacer 2, partial sequence
gi|7546946|gb|AF229461.1|AF229461[7546946]

AF229460

Alternaria alternata strain BMP 21-41-07 internal transcribed spacer 1, partial sequence; 5.8S ribosomal RNA gene, complete sequence; and internal transcribed spacer 2, partial sequence
gi|7546945|gb|AF229460.1|AF229460[7546945]

AF229459

Alternaria alternata strain ATCC 28329 internal transcribed spacer 1, partial sequence; 5.8S ribosomal RNA gene, complete sequence; and internal transcribed spacer 2, partial sequence
gi|7546944|gb|AF229459.1|AF229459[7546944]

AF218791

Alternaria alternata internal transcribed spacer 1, 5.8S ribosomal RNA gene and internal transcribed spacer 2, complete sequence; 28S ribosomal RNA gene, partial sequence; and 18S ribosomal RNA gene, complete sequence
gi|6715474|gb|AF218791.1|AF218791[6715474]

AJ276059

Alternaria alternata 5.8S rRNA gene and ITS 1 and 2, strain MZ20
gi|7208649|emb|AJ276059.1|AAL276059[7208649]

AJ276055

Alternaria alternata 5.8S rRNA gene and ITS 1 and 2, strain MZ7
gi|7208647|emb|AJ276055.1|AAL276055[7208647]

AF071346

Alternaria alternata 18S ribosomal RNA gene, partial sequence; internal transcribed spacer 1, 5.8S ribosomal RNA gene and internal transcribed spacer 2, complete sequence; and 28S ribosomal RNA gene, partial sequence
gi|5031121|gb|AF071346.1|AF071346[5031121]

AF090855

Colletotrichum gloeosporioides internal transcribed spacer 1, 5.8S ribosomal RNA gene and internal transcribed spacer 2, complete sequence; and 28S ribosomal RNA gene, partial sequence
gi|6650331|gb|AF090855.1|AF090855[6650331]

AF065849

Venturia carpophila internal transcribed spacer 1, 5.8S ribosomal RNA gene, and internal transcribed spacer 2, complete sequence
gi|4185734|gb|AF065849.1|AF065849[4185734]

AF090854

Colletotrichum fragariae internal transcribed spacer 1, 5.8S ribosomal RNA gene and internal transcribed spacer 2, complete sequence; and 28S ribosomal RNA gene, partial sequence gi|6650330|gb|AF090854.1|AF090854[6650330]

AF090853

Colletotrichum acutatum 18S ribosomal RNA gene, partial sequence; internal transcribed spacer 1, 5.8S ribosomal RNA gene and internal transcribed spacer 2, complete sequence; and 28S ribosomal RNA gene, partial sequence gi|6650329|gb|AF090853.1|AF090853[6650329]

Z73781

M.fructigena gene for 5.8S ribosomal RNA, internal transcribed spacer 1 and internal transcribed spacer 2 gi|2125846|emb|Z73781.1|MFRUCITSE[2125846]

Z73799

S.sclerotiorum gene for 5.8S ribosomal RNA, internal transcribed spacer 1 and internal transcribed spacer 2 gi|2125909|emb|Z73799.1|SSCLEITSA[2125909]

Z73786

M.laxa gene for 5.8S ribosomal RNA, internal transcribed spacer 1 and internal transcribed spacer 2 gi|2125857|emb|Z73786.1|MLAXAITSC[2125857]

Z73765

B.cinerea gene for 5.8S ribosomal RNA, internal transcribed spacer 1 and internal transcribed spacer 2 gi|2125789|emb|Z73765.1|BCINEITSB[2125789]

What is claimed is:

1. A pair of oligonucleotide primers, consisting of SEQ ID NO: 1 and SEQ ID NO: 27.

2. A method for the detection of *Cladosporium carpophilum*, comprising the steps of:
   (a) isolating DNA from a plant tissue infected with *Cladosporium carpophilum*;
   (b) amplifying a part of the Internal Transcribed Spacer sequence of *Cladosporium carpophilum* using said DNA as a template in a polymerase chain reaction with the pair of primers of claim 1; and
   (c) detecting *Cladosporium carpophilum* by visualizing the amplified part of the Internal Transcribed Spacer sequence.

3. A diagnostic kit used in detecting a fungal pathogen, comprising the primer of primers of claim 1.

* * * * *